United States Patent
Kim et al.

(10) Patent No.: US 10,842,727 B2
(45) Date of Patent: Nov. 24, 2020

(54) COSMETIC COMPOSITION COMPRISING WHITE ROSE FLOWER EXTRACT FOR SKIN WHITENING AND IMPROVING SKIN WRINKLE

(71) Applicants: CHUNGBUK NATIONAL UNIVERSITY INDUSTRY-ACADEMIC COOPERATION FOUNDATION, Cheongju-si (KR); GANGNEUNG-WONJU NATIONAL UNIVERSITY INDUSTRY ACADEMY COOPERATION GROUP, Gangneung-si (KR)

(72) Inventors: Yun-Bae Kim, Cheongju-si (KR); Seong-Soo Joo, Yongin-si (KR)

(73) Assignees: GANGNEUNG-WONGJU NATIONAL UNIVERSITY INDUSTRY ACADEMY COOPERATION GROUP, Gangneung-si (KR); CHUNGBUK NATIONAL UNIVERSITY INDUSTRY-ACADEMIC COOPERATION FOUNDATION, Cheongju-si (KR)

(*) Notice: Subject to any disclaimer, the term of this patent is extended or adjusted under 35 U.S.C. 154(b) by 66 days.

(21) Appl. No.: 16/198,498

(22) Filed: Nov. 21, 2018

(65) Prior Publication Data
US 2019/0105258 A1 Apr. 11, 2019

Related U.S. Application Data

(62) Division of application No. 15/306,331, filed as application No. PCT/KR2014/004984 on Jun. 5, 2014, now abandoned.

(30) Foreign Application Priority Data

Apr. 24, 2014 (KR) .................. 10-2014-0049406

(51) Int. Cl.
*A61K 8/49* (2006.01)
*A61K 8/9789* (2017.01)
(Continued)

(52) U.S. Cl.
CPC ............ *A61K 8/498* (2013.01); *A61K 8/9789* (2017.08); *A61Q 19/02* (2013.01); *A61Q 19/08* (2013.01); *A61K 2800/782* (2013.01)

(58) Field of Classification Search
None
See application file for complete search history.

(56) References Cited

U.S. PATENT DOCUMENTS

2003/0138467 A1 7/2003 Ptchelintsev
2006/0110415 A1 5/2006 Gupta

FOREIGN PATENT DOCUMENTS

KR 10-2002-0062513 A 7/2002
KR 10-2006-0101100 A 9/2006
(Continued)

OTHER PUBLICATIONS

Machine translation, KR 10-2011-0072153 (2011).*
(Continued)

*Primary Examiner* — Bethany P Barham
*Assistant Examiner* — Barbara S Frazier
(74) *Attorney, Agent, or Firm* — Nixon & Vanderhye P.C.

(57) ABSTRACT

Provided is a functional cosmetic composition of white rose extract and a gartanin derivative compound isolated therefrom, and specifically, to a cosmetic composition for skin whitening and skin wrinkle alleviation containing, as active ingredients, white rose petal extract and gartanin derivative (Continued)

compounds isolated therefrom. The white rose extract and gartanin derivative compound, according to the present invention, are safe without causing side effects on the skin, prevent melanin production through a mechanism inhibiting tyrosinase activity, thereby having a whitening effect, and exhibit a wrinkle alleviation effect by a mechanism inhibiting MMP-1 activity, and thus the composition, of the present invention, containing the same as active ingredients, can be utilized as a material for functional cosmetics for skin whitening and wrinkle alleviation without causing skin irritation.

5 Claims, 6 Drawing Sheets

(51) Int. Cl.
*A61Q 19/02* (2006.01)
*A61Q 19/08* (2006.01)

(56) References Cited

FOREIGN PATENT DOCUMENTS

KR  10-2008-0072122 A  8/2008
KR  10-2011-0072153 A  6/2011

OTHER PUBLICATIONS

Machine translation, KR 10-2006-0101100 (2006).*
Kim, E.-H., "A Study of Whitening Cosmetics from natural products," vol. 4 No. 2, pp. 195-203, 2006. Abstract.
PCT International Search Report dated Jan. 20, 2015 for PCT/KR2014/004984 filed Jun. 5, 2014, Title: "Cosmetic Composition for Skin Whitening and Wrinkle Alleviation, Containing, as Active Ingredients, White Rose Extract and Gartanin Derivative Compound Isolated Therefrom,".

* cited by examiner

[Fig. 1]
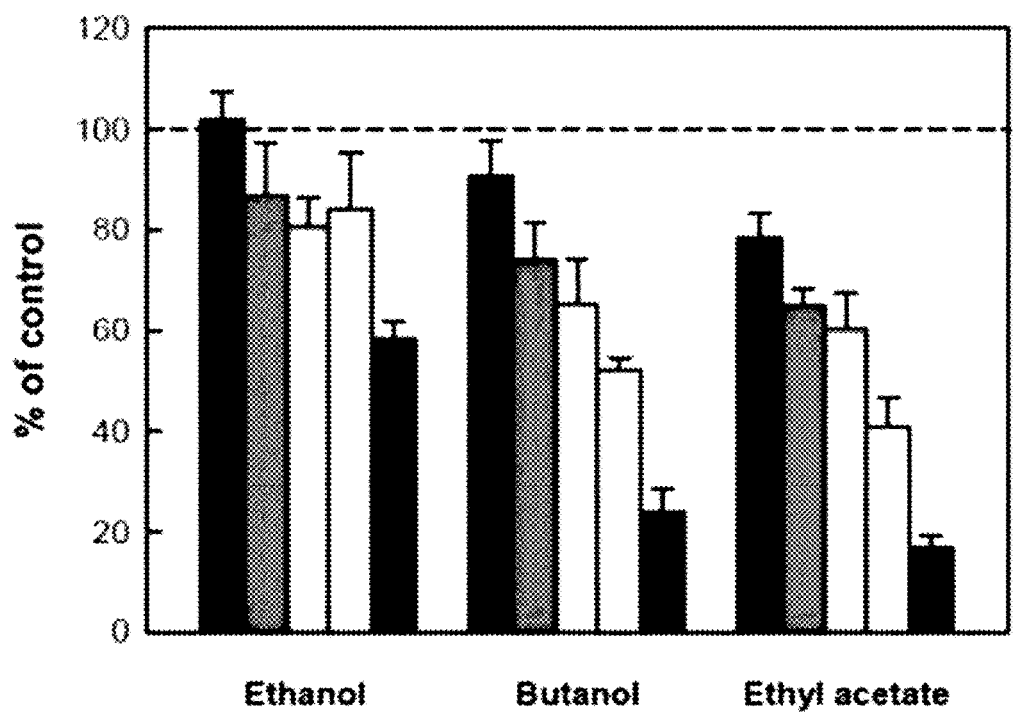
[Fig. 2]
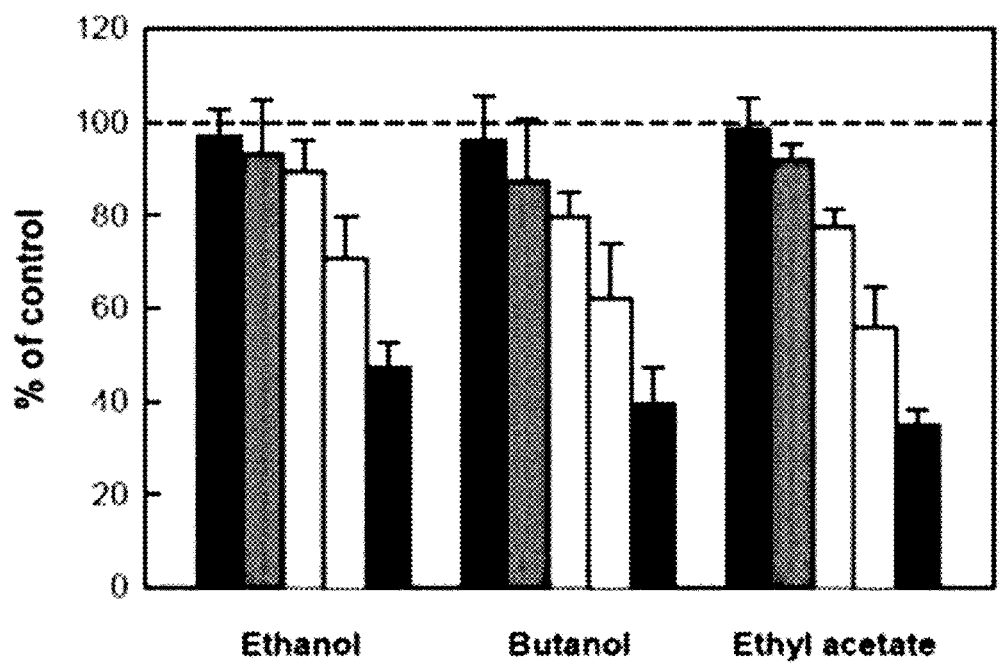

[Fig. 3]
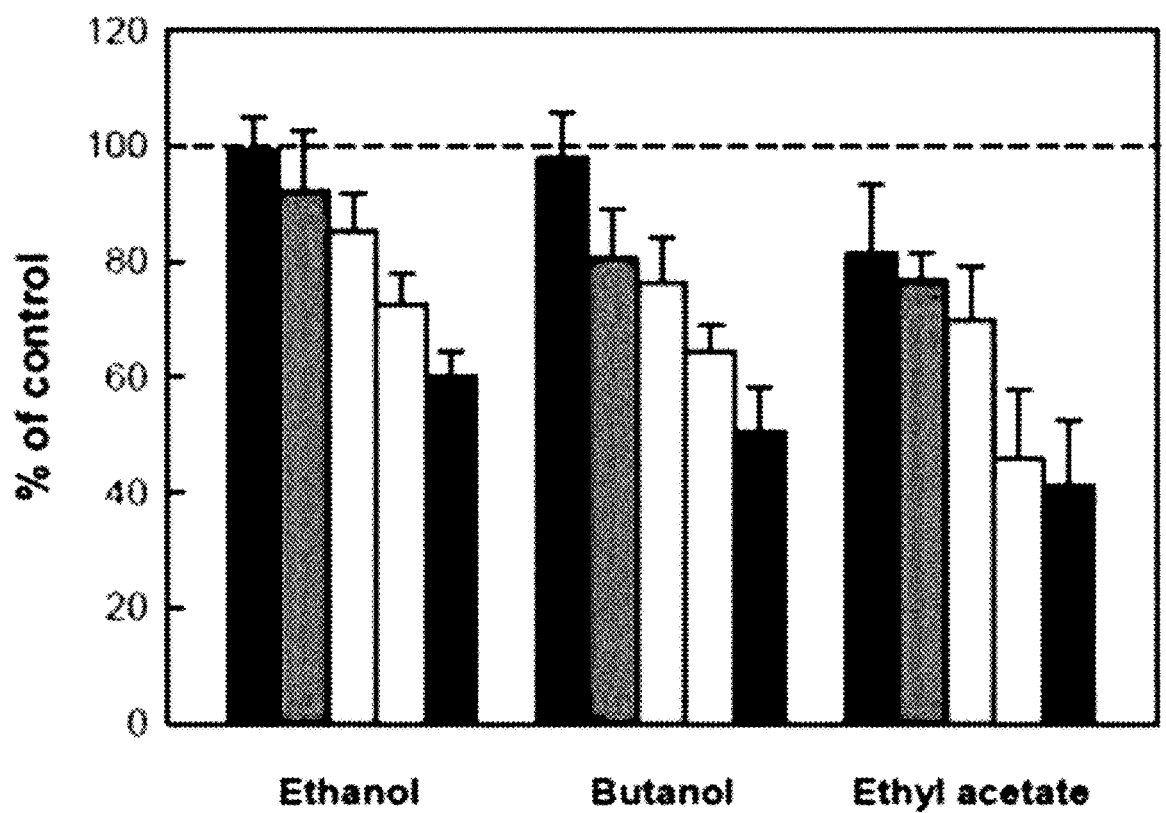

[FIG 4]
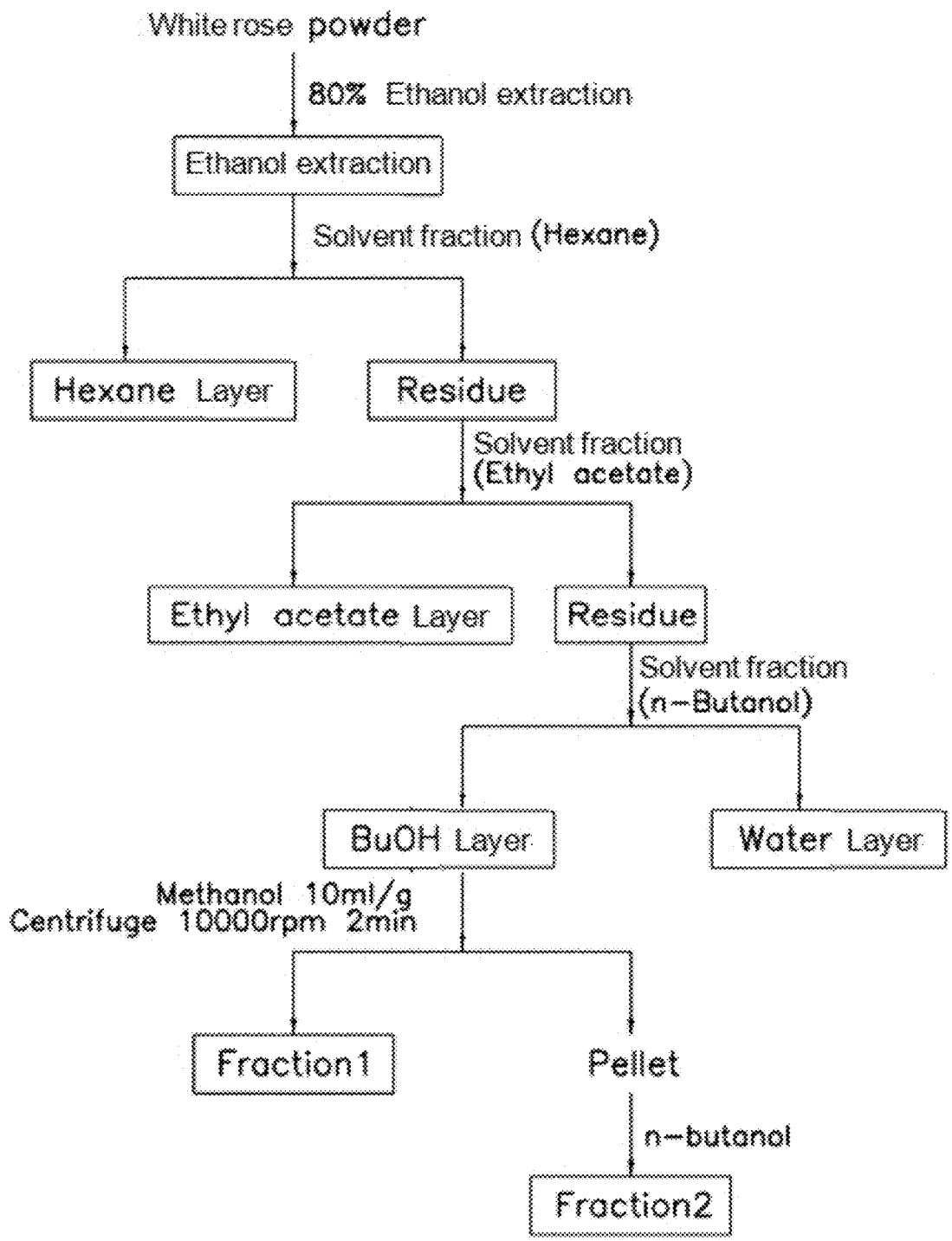

[Fig. 5]
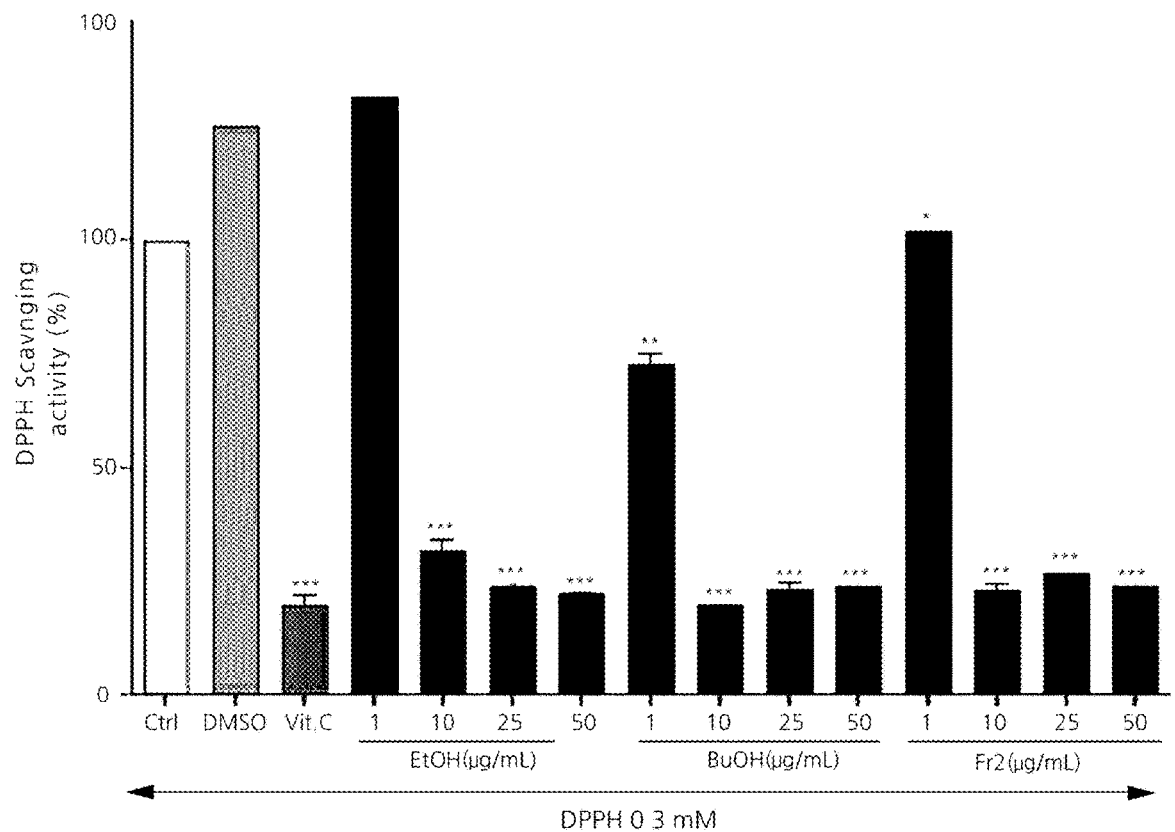

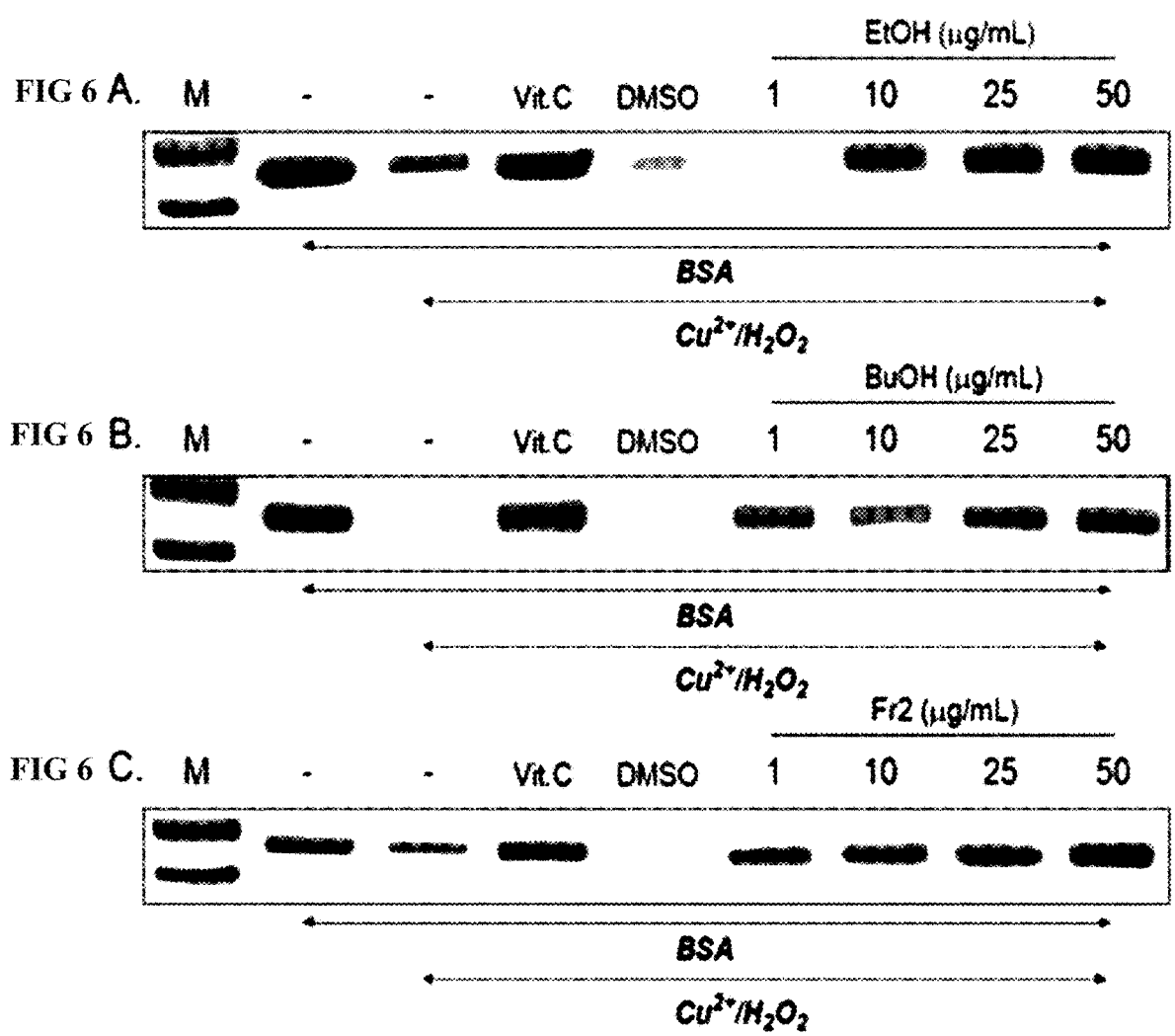

[Fig. 7]
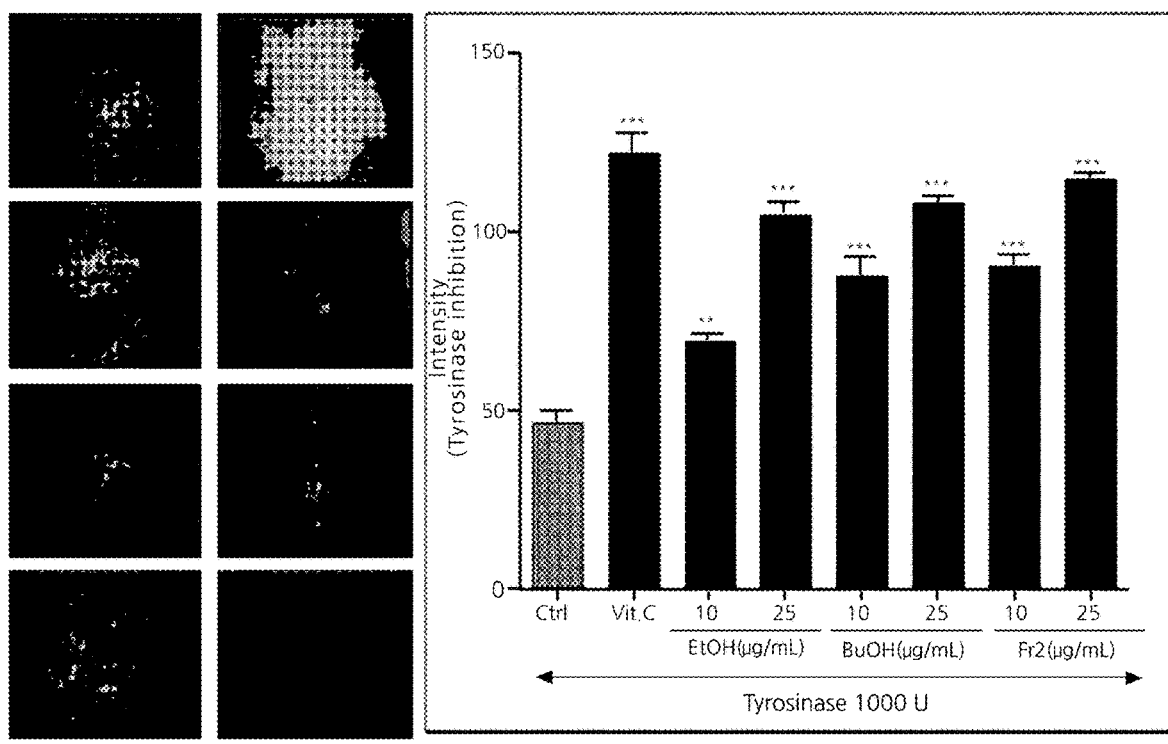

COSMETIC COMPOSITION COMPRISING WHITE ROSE FLOWER EXTRACT FOR SKIN WHITENING AND IMPROVING SKIN WRINKLE

TECHNICAL FIELD

The present invention relates to a functional cosmetic composition including, as an active ingredient, white rose extract, and more particularly, to a functional cosmetic composition having skin whitening and wrinkle alleviation functions including, as an active ingredient, white rose extract.

BACKGROUND ART

The skin is a defense organ on the front line of the human body which protects the body from external stimuli and even from the aesthetic point of view, an interest thereof has been gradually increased. Accordingly, studies on a variety of functional cosmetics are actively conducted and among the studies, various functional cosmetics for wrinkle alleviation and whitening functions are being launched.

Skin aging is largely divided into two types of intrinsic aging and extrinsic aging according to a cause thereof. The intrinsic aging is an aging process which is naturally caused while a physiological function of the living body is deteriorated as the age increases and the extrinsic aging is an aging process generated by external factors such as ultraviolet (UV), dry air, reactive oxygen species, and stress. When the skin aging is in progress by these factors, wrinkle is generated on the skin surface.

Various causes of the wrinkle generation have been reported and first, when the skin is exposed to excessive UV, decomposition of collagen as a skin ingredient is accelerated and thus the skin elasticity is lost and the wrinkle may be generated. Further, when the skin is excessively dried by an excessive change in temperature, a decrease in humidity, wind, or the like, the skin function as a barrier to the outside is deteriorated and the wrinkle is generated. In addition, when the skin is exposed to reactive oxygen species or free radicals, lipid peroxides are produced by oxidation and as a result, skin structural proteins such as collagen are deformed and the wrinkle may be generated.

Meanwhile, when the skin aging occurs, cornification of the skin occurs, a fusion rate of epidermal cells is gradually decreased, an epidermal cell layer is thinned, the cornified layer is thickened, and a boundary with the dermal layer becomes in a straight line. In the corium, as human skin fibroblasts are aged, productivity of fibers and the matrix is reduced, intracellular peroxide levels rapidly increase, the function of the cells cannot be smoothly performed and the metabolic activity of the cells is reduced under the influence of various types of pollutants and stress. As a result, the wrinkle is generated due to functional and structural damages and thus the skin aging is accelerated. Accordingly, various cosmetic compositions to prevent skin aging or wrinkle generation caused by the external factor and the internal factors have been studied.

Meanwhile, when the UV is irradiated to the skin, melanocytes in the skin are activated and thus melanin production is accelerated by action of enzyme tyrosinase, TRP1, and TRP2. The produced melanin is pigmented in the skin to be developed to "age spots" and "freckles" and in order to prevent the age spots and the freckles, whitening cosmetics including various cosmetic compositions have been used. Further, it is known that the UV accelerates sebum, oxidation of a cell membrane and the like to cause various skin disorders, and particularly, recently, more effectively preventive measures of skin oxidation caused by an increase in UV according to depletion of the ozone layer have been required.

Ingredients having a whitening effect which are known in the related art include ascorbic phosphate ester salts, hydroquinone derivatives, placenta extracts, kojic acid, ellagic acid, and the like, and cosmetic compositions mixing these ingredients are general. Particularly, in recent years, whitening cosmetics using the placenta extracts have been in the limelight, but in the placenta extracts, the supply amount is limited and the use there is limited in a combination of ethical issues. Accordingly, an interest in the development of novel and effective whitening ingredients has been focused.

In recent years, it is reported that polyphenol and the like included in the plant have a high whitening effect and cosmetic compositions using the polyphenol and the like have been proposed. Further, the whitening effect of flavanones and hydroxy flavones is already disclosed. However, in these whitening ingredients, the effect thereof is somewhat minimal and there is a problem during storage, and a wrinkle prevention effect and an aging prevention effect in addition to the whitening effect are not sufficiently exhibited. Particularly, there is a problem in that functional cosmetics including chemical ingredients cause skin irritation and are not suitable for sensitive skin, and an interest in functional cosmetics having small stimuli to the skin and derived from eco-friendly natural plants has been focused.

Meanwhile, a white rose flower includes, as an active ingredient, a white rose extract in the related art as a species belonging to the genus Rose, and effects such as anti-oxidation, anti-inflammatory, and anti-allergy are already disclosed, but skin whitening and wrinkle alleviation effects on the white rose flower are not yet studied.

Therefore, the inventors tested functions by focusing on a white rose extract while seeking a natural substance as a novel material for preparing cosmetics with excellent skin whitening and wrinkle alleviation effects without side effects to the living body. As a result, the inventors found that an ethanol extract of the white rose effectively inhibited activity of tyrosinase in vitro to have a whitening effect and effectively inhibited activity of collagenase to have a wrinkle alleviation function and completed the present invention.

DISCLOSURE

Technical Problem

The present invention is directed to provide a functional cosmetic composition having skin whitening and skin wrinkle alleviation effects without having side effects in the body.

Technical Solution

One aspect of the present invention provides a cosmetic composition for skin whitening or skin wrinkle alleviation including a white rose extract as an active ingredient.

The white rose extract may be an extract obtained by extracting dried white rose petal with ethanol, butanol, or ethyl acetate.

The white rose extract may prevent melanin production by suppressing or inhibiting activity of tyrosinase.

The white rose extract may improve skin elasticity by suppressing or inhibiting activity of MMP-1.

Another aspect of the present invention provides a cosmetic composition for skin whitening or skin wrinkle alleviation including 3,5-di-o-methyl-gartanin as an active ingredient.

The 3,5-di-o-methyl-gartanin may be isolated from at least one rose selected from the group consisting of white rose flower, Red Sandra, Red Velvet, First Red, Nobless, Konffetti, My Heart, Grand Gala, Dolores, Rote Rose, Saphir, Mercedes, Gabriella, Frisco, Only Love, Coco, Escimo, Calibra, Mimi Rose, Little Mable, Princess, Evelien and Chaming.

The 3,5-di-o-methyl-gartanin may be derived from the white rose petal extract.

The 3,5-di-o-methyl-gartanin may prevent melanin production by suppressing or inhibiting activity of tyrosinase.

The 3,5-di-o-methyl-gartanin may improve skin elasticity by suppressing or inhibiting activity of MMP-1.

The composition may be formulated by at least one selected from the group consisting of skin lotion, skin softener, skin toner, astringent, lotion, milk lotion, moisturizing lotion, nutrition lotion, massage cream, nourishing cream, moisturizing cream, hand cream, essence, nutrition essence, pack, soap, shampoo, cleansing foam, cleansing lotions, cleansing cream, body lotion, body cleanser, emulsion, lipstick, makeup base, foundation, pressed powder and loose powder.

Advantageous Effects 3,5-di-o-methyl-gartanin derived from a white rose petal extract or white rose petal has a whitening effect by suppressing melanin production through a mechanism of inhibiting tyrosinase activity and has effects of enhancing skin elasticity and alleviating a wrinkle through a mechanism of inhibiting activity of MMP-1. Therefore, the composition of the present invention including 3,5-di-o-methyl-gartanin as an active ingredient can be utilized as a material for functional cosmetics for skin whitening and skin wrinkle alleviation without causing skin irritation.

DESCRIPTION OF DRAWINGS

FIG. 1 is a result of observing an MMP-1 inhibitory effect for an extract obtained by extracting white rose petal with ethanol, butanol, and ethyl acetate (black: 1 μg/mL, red: 3.2 μg/mL, green: 10 μg/mL, yellow: 32 μg/mL, and blue: 100 μg/mL).

FIG. 2 is a result of observing a tyrosinase inhibitory effect for an extract obtained by extracting white rose petal with ethanol, butanol, and ethyl acetate (black: 1 μg/mL, red: 3.2 μg/mL, green: 10 μg/mL, yellow: 32 μg/mL, and blue: 100 μg/mL).

FIG. 3 is a result of observing a melanin synthesis inhibitory effect for an extract obtained by extracting white rose petal with ethanol, butanol, and ethyl acetate (black: 1 μg/mL, red: 3.2 μg/mL, green: 10 μg/mL, yellow: 32 μg/mL, and blue: 100 μg/mL).

FIG. 4 is a result illustrating a process of preparing white rose petal fractions of the present invention.

FIG. 5 is a result of measuring DPPH radical scavenging activity for each treatment concentration with respect to extracts of the white rose petal extracted with ethanol, butanol, and fraction 2.

FIGS. 6A, 6B and 6C show results of performing a metal ion catalytic oxidation inhibition test for each treatment concentration with respect to extracts of the white rose petal extracted with ethanol, butanol, and fraction 2.

FIG. 7 is a result of measuring tyrosinase activity for each treatment concentration with respect to extracts of the white rose petal extracted with ethanol, butanol, and fraction 2.

MODES OF THE INVENTION

While the inventors studied a novel cosmetic material capable of preventing skin aging, alleviating skin wrinkle, and enhancing a skin whitening effect, the inventors verified that a white rose petal extract had the functions.

Therefore, the present invention is characterized by providing a functional cosmetic composition including, an active ingredient, a white rose petal extract extracted from white rose petal.

Particularly, while the inventors was trying to find a material having an excellent whitening effect and anti-aging effect while being derived from a natural material to be stable in the human body, the inventors paid attention to a white rose extract and verified that the white rose petal extract had a whitening effect and a wrinkle alleviation effect through an experiment.

That is, according to an exemplary embodiment of the present invention, it is exhibited that the white rose extract suppresses or inhibits activity of MMP-1 to improve skin elasticity (see FIG. 1).

Meanwhile, melanin as a pigment present in the skin has an important function of protect a body from external stimuli such as UV rays. However, when the melanin is excessively produced to be pigmented, the melanin forms age spots, freckles, or the like to cause skin appearance problems, and furthermore, facilitate skin aging and cause skin cancer, and thus a material capable of suppressing over-production of the melanin can be used as a whitening product.

It is known that skin pigmentation is caused by stimuli such as UV or inflammation and generated by genetic factors or factors such as hormones, chemicals, foods, and the like. Skin melanocytes are involved in a biosynthesis process of melanin. That is, the biosynthesis of the melanin occurs in a specific-shaped small organ in melanocytes called melanosome and an enzyme called tyrosinase plays the most important role in generation of the melanin in the melanosome. Tyrosine is converted to dopa by action of the enzyme, generated to dopaquinone through a series of oxidation processes, and converted to dopachrome again to finally form dark-brown melanin. The expression of tyrosinase, tyrosinase related protein-1 (TRP-1), TRP-2, and extracellular signal-regulated kinases (ERK) as protein genes involved in formation of the melanin pigment and a microphthalmia-associated transcription factor (MITF) which is a main transcription factor regulating expression of the melanin synthesis plays an important role in a melanin synthesis process.

According to an exemplary embodiment of the present invention, it is exhibited that the white rose petal extract of the present invention inhibits tyrosinase concentration-dependent to have activity of suppressing melanin synthesis (see FIGS. 2 and 3).

Accordingly, the white rose petal extract of the present invention of suppressing the tyrosinase activity may be used for preventing skin pigmentation and a skin whitening effect.

Through such a result, the inventors were experimentally verified that the white rose petal extract of the present invention has both the skin wrinkle alleviation effect and the skin whitening effect.

Meanwhile, the inventors additionally experimented whether any component of the white rose petal extract particularly has the skin wrinkle alleviation effect and the skin whitening effect.

As a result, it was verified that 3,5-di-o-methyl-gartanin corresponding to a 14-th peak of a fraction obtained by extracting white rose petal with butanol has the best MMP-1 activity inhibition and tyrosinase activity inhibition.

Accordingly, the present invention may provide a cosmetic composition for skin whitening and skin wrinkle alleviation including, as active ingredients, 3,5-di-o-methyl-gartanin in addition to the white rose petal extract.

The white rose extract according to the present invention may use an extract extracted and isolated from a natural material by using extraction and isolation methods which are known in the art. The "extract" defined in the present invention is extracted from white rose by using an appropriate solvent and for example, includes all of a crude extract, a polar solvent soluble extract, and a non-polar solvent soluble extract of the white rose. Preferably, the white rose extract may be an extract extracted from white rose petal.

An appropriate solvent for extracting the extract from the white rose may use any pharmaceutically acceptable organic solvent and may use water or an organic solvent, but is not limited thereto. For example, the solvent may use various solvents including purified water, alcohols of carbon atoms 1 to 4 including methanol, ethanol, propanol, isopropanol, butanol, and the like, acetone, ether, benzene, chloroform, ethyl acetate, methylene chloride, hexane, cyclohexane, and the like, alone or in combination. Preferably, the solvent may use ethanol (alcohol), butanol, or ethyl acetate.

The extraction method may use any one selected from methods including hot water extraction, chilling extraction, reflux cooling extraction, solvent extraction, steam distillation, ultrasonic extraction, elution, pressing, and the like. Further, a desired extract may additionally perform a general fraction process and be purified by using a general purification method. The method of preparing the white rose extract of the present invention is not limited and may use any known method.

For example, in the white rose extract included in the composition of the present invention, a primary extract extracted by the hot water extraction or solvent extraction may be prepared in a powder state by an additional process such as vacuum distillation and freeze drying or spray drying. Further, the primary extract may obtain additionally purified fractions by using various chromatography including silica gel column chromatography, thin layer chromatography, high performance liquid chromatography, and the like.

Accordingly, in the present invention, the white rose extract is a concept including all of extracts, fractioned and purified materials, their dilutions, concentrates, or dried materials which are obtained in each step of extraction, fraction, or purification.

The method of preparing the white rose extract according to the exemplary embodiment of the present invention will be described below in more detail.

In the present invention, the dried white rose petal is grinded and powdered and then extracted for 24 hours at room temperature by adding ethanol or water to the powder. Thereafter, the water extract is additionally deposited with butanol or ethyl acetate for 24 hours at room temperature again to obtain the white rose petal extract through a process which is prepared to the freeze-dried powder.

Further, 100 mg of the butanol extract is centrifuged for 2 minutes at 10,000 rpm after adding 1 ml of methanol and F2 fractioned by adding 1 ml of butanol to the precipitated pellet is analyzed by using GC/MS (agilent technologies 5975C), and as a result, 3,5-di-o-methyl-gartanin may be obtained through a 14-th solvent peak.

As such, when the extract extracted from the white rose petal or a compound purified therefrom is prepared by the cosmetic composition, the composition of the present invention may include ingredients generally used in the cosmetic composition in addition to the aforementioned white rose petal extract, for example, general additives, such as anti-oxidants, stabilizers, solubilizers, vitamins, pigments and perfumes, and carriers.

Further, the composition of the present invention may be used by combining an organic sunscreen which has been used from the past to the extent that a skin protection effect is not damaged by reacting with the white rose petal extract other than the aforementioned white rose petal extract.

The organic sunscreen may use at least one selected from the group consisting of glyceryl PABA, drometrizole trisiloxane, drometrizole, digalloyl trioleate, disodium phenyl dibenzimidazole tetrasulfonate, diethylhexyl butamido triazone, diethylamino hydroxybenzoyl hexyl benzoate, DEA-methoxylcinnamate, a mixture of lawsone and dihydroxyl acetone, methylene bis-benzotriazolyl tetramethylbutylphenol, 4-methylbenzylidene camphor, menthyl anthranilate, benzophenone-3 (oxybenzone), benzophenone-4, benzophenone-8 (dioxyphebenzone), butyl methoxydibenzoylmethane, bis-ethylhexyloxyphenolmeth oxyphenyltriazine, cinoxate, ethyldihydroxypropyl PABA, cctocrylene, ethylhexyl dimethyl PABA, ethylhexyl methoxycinnamate, ethylhexyl salicylate, ethylhexyl triazone, isoamyl p-methoxycinnamate, polysilicon-15 (dimethicodiethylbenzal malonate), terephthalylidene dicamphor sulfonic acid and its salts, TEA salicylate, and amino benzoic acid (PABA).

Further, the cosmetic composition of the present invention may be prepared by any formulation which is generally prepared in the art and for example, may be formulated by a solution, a suspension, an emulsion, paste, gel, cream, lotion, powder, soap, a surfactant-containing cleanser, oil, powder foundation, emulsion foundation, wax foundation, spray and the like, but is not limited thereto. More particularly, the cosmetic composition of the present invention may be prepared by formulation of emulsion lotion, nutrition lotion, nourishing cream, massage cream, essence, eye cream, cleansing cream, cleansing foam, cleansing water, pack, spray or powder.

When the formulation of the present invention is paste, cream, or gel, as a carrier ingredient, animal oil, vegetable oil, waxes, paraffins, starch, tragacanth, cellulose derivatives, polyethylene glycols, silicones, bentonites, silica, talc, zinc oxide, or the like may be used.

When the formulation of the present invention is the solution or the emulsion, as a carrier ingredient, a solvent, a dissolving agent, or an emulsifying agent is used, and for example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or sorbitan fatty acid ester is included.

When the formulation of the present invention is the suspension, as the carrier ingredient, a liquid diluent, such as water, ethanol, or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar or tragacanth may be used.

When the formulation of the present invention is the powder or the spray, as the carrier ingredient, lactose, talc, silica, aluminum hydroxide, calcium silicate, or polyamide powder may be used. Particularly, in the case of the spray, a propellant such as chloro-fluoro hydrocarbon, propane/butane or dimethyl ether may be additionally included.

When the formulation of the present invention is the surfactant-containing cleanser, as the carrier ingredient, aliphatic alcohol sulfate, aliphatic alcohol ether sulfate, sulfosuccinate monoester, isethionate, imidazolinium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, ethoxylated glycerol fatty acid ester, or the like may be used.

Further, the present invention may provide a make-up method having a skin aging prevention, skin wrinkle alleviation, or skin whitening effect by applying a cosmetic composition including, as an active ingredient, a white rose petal extract or 3,5-di-o-methyl-gartanin to the human skin.

The make-up method of the present invention refers to all make-up methods using the cosmetic composition of the present invention. That is, all of the methods which are known in the art using the cosmetic composition belong to the make-up method of the present invention.

The cosmetic composition of the present invention is used alone or in duplicate or may be used by duplicating other cosmetic compositions other than the cosmetic composition of the present invention. Further, the cosmetic composition according to the present invention may be used according to a general use method and vary the number of uses according to a skin state or a taste of a user.

When the cosmetic composition of the present invention is soap, surfactant-containing cleansing formulation or a surfactant-free cleansing formulation, the cosmetic composition is coated on the skin and then wiped or removed or cleaned with water. As a particular example, the soap is liquid soap, powder soap, solid soap and oil soap, the surfactant-containing cleansing formulation is cleansing foam, cleansing water, a cleansing towel and a cleansing pack, and the surfactant-free cleansing formulation is cleansing cream, cleansing lotion, cleansing water and cleansing gel, and the present invention is not limited thereto.

Hereinafter, the present invention will be described in more detail by Examples. These Examples are just to describe the present invention in more detail and it is apparent to those skilled in the art that the scope of the present invention is not limited to these Examples.

Example 1

Preparation of White Rose Petal

The white rose petal used in the present invention was collected at Jincheon, Chungbuk, Korea in May, 2010 and then completely dried under the sun and used. The completely dried petal was grinded and powdered by using a rotor speed mill (Laval Lab Inc., Laval, Que), sterilized by using a 70% ethanol spray, dried at 80° C., and then stored at 4° C. before usage.

Example 2

Preparation of White Rose Petal Extract

The prepared dried white rose petal powder was divided into two parts and extracted with ethanol or water.

First, the ethanol extract was deposited by using 70% ethanol 10 times larger than a volume of the white rose petal powder and extracted for 24 hours at room temperature. An extracted suspension was filtered by a Whattman filter (No. 1) and the filtrate was concentrated under a vacuum at 50° C. and freeze-dried to obtain the extract. Samples obtained from the ethanol extract were continuously fractioned through n-hexane ethyl acetat (EA), chloroform, n-butanol (BuOH), and distilled water, and the obtained fractions were dried by an evaporator. Then, the obtained products were used for the experiments.

Example 3

Analysis of Collagen Matrix Metalloproteinase-1 Inhibitory Effect of White Rose Petal Extract As part of measuring a wrinkle alleviation effect of the white rose petal extract, effects of inhibiting activity of collagen matrix metalloproteinase-1 (MMP-1) of the extracts were measured with reference to the guideline of "beauty-related functional tests (pp. 821-858)" of Korea health official compendium research society foundation.

When simply describing the effect, 25 mg of bovine tendon collagen was dissolved in a 0.05 M tris(hydroxymethyl)-methyl-2-aminoethane sulfonate (TES) buffer and then left for 15 minutes at 37° C. Next, a test material for each concentration was added and then additionally reacted with collagenase type-1 for 5 hours at 37° C. 0.2 mL of a reaction solution was taken and added to 1 mL of a buffer [4% ninhydrin in methyl cellosolve (2-methoxyethanol)+0.2 M sodium citrate with 0.71 mM stannous chloride]. The reaction solution was boiled for 20 minutes, added with n-propanol, and then left for 15 minutes and then absorbance was measured at 600 nm. On the basis of a change in absorbance when only the buffer without the white rose fractions was added as a reference (100%), reduction of the absorbance caused by the white rose fractions for each concentration was represented by an inhibition rate.

As a result, as illustrated in FIG. 1, the ethanol fraction exhibited a MMP-1 activity inhibition rate of 41.7% in 100 μg/mL, and the butanol fraction exhibited the MMP-1 activity inhibition rate of 34.9% in 10 μg/mL, 47.7% in 32 μg/mL, and 76.1% in 100 μg/mL. Meanwhile, the ethyl acetate fraction had the strongest MMP-1 activity inhibition effect and exhibited the inhibition rate of 35.0% in 3.2 μg/mL, 39.8% in 10 μg/mL, 59.0% in 32 μg/mL, and 83.1% in 100 μg/mL.

Through the above result, the inventors verified that all of the ethanol extract, the butanol extract, and the ethyl acetate extract of the white rose petal inhibited the activity of MMP-1. Accordingly, it can be seen that the ethanol extract, the butanol extract, and the ethyl acetate extract of the white rose petal have an excellent wrinkle alleviation effect.

Example 4

Analysis of Melanin Synthase (Tyrosinase) Inhibitory Effect of White Rose Petal Extract Meanwhile, in order to measure a skin whitening effect of the white rose petal extract, an effect of inhibiting activity of tyrosinase as melanin synthase was measured with reference to the guideline of "beauty-related functional tests (pp. 821-858)" of Korea health official compendium research society foundation.

When simply describing this, 20 μL of mushroom tyrosinase (2,000 unit/mg) and 10 μL of 10 mM L-dihydroxyphenylalanine (L-DOPA) were added in 70 μL of a white rose fraction sample (1, 3.2, 10, 32, 100 μg/mL of final concentrations) dissolved in PBS (pH 6.8) on each well of a 96-well plate and then reacted for 30 minutes at 37° C., and absorbance at 475 nm was measured by using a microplate reader (Infinite 200, Tecan Group Ltd., Switzerland). In this case, on the basis of a change in absorbance when only the buffer without the white rose fractions was added as a reference (100%), reduction of the absorbance caused by the white rose fractions for each concentration was represented by an inhibition rate.

As a result, as illustrated in FIG. 2, the ethanol fraction exhibited a tyrosinase inhibition rate of 29.4% in 32 μg/mL and 52.9% in 100 μg/mL, and the butanol fraction exhibited the tyrosinase inhibition rate of 38.1% in 32 μg/mL, and 60.4% in 100 μg/mL. Meanwhile, it was verified that the ethyl acetate fraction exhibited the strongest tyrosinase inhibition rate and exhibited a tyrosinase inhibition rate of 44.3% in 32 μg/mL and 65.1% in 100 μg/mL.

Example 5

Analysis of Melanin Synthesis Inhibitory Effect of White Rose Petal Extract

In order to more definitize a skin whitening effect of the white rose petal extract, the inventors measured a melanin synthesis inhibitory effect of the white rose petal extract at a cell level with reference to the guideline of "beauty-related functional tests (pp. 821-858)" of Korea health official compendium research society foundation (2004).

When simply describing this, B16 mouse melanoma cells were dispensed to $1\times10^4$ cells/well (0.5 mL) in a 96-well plate and cultured for 24 hours. The B16 mouse melanoma cells was treated with the white rose fraction for each concentration and a α-melanocyte stimulating hormone (MSH) and additionally cultured for 3 days at 37° C. The cells were lysed by adding 0.15 mL of 1 M NaOH to a culture medium and boiled for 5 minutes to elute the melanin. 0.1 mL of the eluate was taken and absorbance at 490 nm was measured. A standard calibration curve was created by synthetic melanin and the concentration was quantified and an inhibition rate for each concentration of the white rose fraction was proposed based on a melanin production amount when the sample was not treated as a reference (100%).

As a result, as illustrated in FIG. 3, the ethanol fraction exhibited a melanin synthesis inhibition rate of 27.7% in 32 μg/mL and 39.9% in 100 μg/mL, and the butanol fraction exhibited the melanin synthesis inhibition rate of 23.5% in 10 μg/mL, 35.5% in 32 μg/mL, and 49.6% in 100 μg/mL. Meanwhile, the ethyl acetate fraction exhibited the strongest melanin synthesis inhibition rate and exhibited the melanin synthesis inhibition rate of 30.2% in 10 μg/mL, 54.4% in 32 μg/mL, and 58.8% in 100 μg/mL.

Through the result, the inventors verified that all of the ethanol extract, the butanol extract, and the ethyl acetate extract of the white rose petal inhibited the activity of the tyrosinase and suppressed the melanin synthesis. Accordingly, it can be seen that the ethanol extract, the butanol extract, and the ethyl acetate extract of the white rose petal exhibit the excellent whitening effect.

Example 6

Ingredient Analysis of White Rose Petal Extract

The inventors analyzed specific ingredients of the white rose petal extract having the wrinkle alleviation and whitening effects. To this end, the inventors isolated a supernatant (fraction 1, 75%, hereinafter, referred to as 'F1') by adding 1 ml of methanol to 100 mg of the butanol extract and then the centrifuging the butanol extract for 2 minutes at 10000 rpm and obtained fraction 2 (8%, hereinafter, referred to as 'F2') by adding 1 ml of butanol to the precipitated pellet (See FIG. 4).

The F1 and F2 were analyzed by using GC/MS (Agilent Technologies 5975C) installed with a CTC CombiPAL autosampler system (Palo Alto, Calif., USA). A column used in sample analysis was a HP-5 column (Agilent Technologies, 250 μm×0.25 μm×30 m) and 10 μL of the sample was analyzed. An injector temperature was 250° C. and was measured up to 280° C. at an interval of 3° C. per minute after a GC oven stopped for 5 minutes at 50° C. Data from after 4 minutes was collected by considering a solvent peak and Wiley7N library data were used for ingredient analysis.

As a result, ingredients in the following Tables 1 and 2 could be verified.

TABLE 1

Ingredient Analysis Table of F1

| Peak | Retention time | Fraction 1 | % Area | Quality |
|---|---|---|---|---|
| 1 | 6.448 | 2-Methyl-2-butanal | 0.37 | 33 |
| 2 | 7.518 | Furfural | 5.60 | 64 |
| 3 | 7.701 | 1,5-Dimethyl-1H-pyrazole | 0.13 | 86 |
| 4 | 8.192 | 2,5-Furandione | 0.19 | 86 |
| 5 | 12.249 | 4-Oxo-5-methoxy-2-penten-5-olide | 0.27 | 86 |
| 6 | 12.500 | 5-methyl-2-furancarboxaldehyde | 0.38 | 95 |
| 7 | 13.165 | 1-Methoxy-difluorobenzene | 0.20 | 38 |
| 8 | 13.878 | 3-Acetyldihydro-2(3H)-furanone | 0.18 | 50 |
| 9 | 14.572 | Propynamide | 0.16 | 37 |
| 10 | 16.113 | 3-Fluoro-1,2-benzenediol | 0.40 | 27 |
| 11 | 16.219 | 4-Ethyl-cyclohexanone | 0.12 | 30 |
| 12 | 16.297 | 4-Oxo-pentanoic acid | 0.37 | 14 |
| 13 | 17.646 | 2-Methoxy-6-methyl-pyrazine | 0.10 | 74 |
| 14 | 18.147 | 3-Hydroxy-5-methyl-4H-pyran-4-one | 0.18 | 35 |
| 15 | 19.322 | 2-Furanmethanol | 0.26 | 86 |
| 16 | 20.084 | 5-Methyl-2(3H)-furanone | 0.12 | 30 |
| 17 | 21.028 | 2,3-Dihydro-3,5-dihydroxy-6-methyl-4H-pyran-4-one | 0.89 | 90 |
| 18 | 23.630 | 2-Butyl-4,5-dimethyloxazole | 0.24 | 38 |
| 19 | 23.909 | Butanedioic acid | 0.43 | 27 |
| 20 | 24.256 | 3,4,5,6-Dibenzocarbazole | 2.29 | 50 |
| 21 | 24.661 | 2-Methyl-cycloheptanone | 0.45 | 30 |
| 22 | 24.941 | 5-(hydroxymethyl)-2-Furancarboxaldehyde | 31.56 | 91 |
| 23 | 29.624 | 1-(3-Chloro-2-propenyl)-4-methoxy benzene | 0.58 | 30 |
| 24 | 29.778 | 1-Fluoro-3(2-cyanoethenyl)-benzene | 0.62 | 22 |
| 25 | 29.971 | 4-Methoxy-benzeneacetonitrile | 1.05 | 46 |
| 26 | 30.000 | 1a,2,3,5-tetrahydro-1H-cycloprop[c]indol-5-one | 1.28 | 47 |
| 27 | 30.858 | 1,3-cyclopentadione | 0.53 | 30 |
| 28 | 31.330 | 1,2,3-Benzenetriol | 40.38 | 95 |
| 29 | 40.195 | Harmin | 0.17 | 47 |
| 30 | 40.234 | 1,2-Dihydro-7,12-methano-4H-cyclodeca[c]pyran-4-one | 0.11 | 64 |
| 31 | 40.330 | Tetrahydroanthraquinone | 0.09 | 64 |
| 32 | 40.542 | (E)-2,4'-dihydroxystilbene | 0.66 | 64 |
| 33 | 40.610 | [2.2](2,6)pyrazinophane | 0.24 | 83 |
|  |  | (E)-2,2'-stilbenediol |  | 50 |
| 34 | 40.976 | 1-(4-Pyrroylcarbonyl)benzotriazole | 3.49 | 43 |
| 35 | 41.988 | (Z)-1,2-Difluoro-1-(p-methoxyphenyl)ethene | 0.58 | 50 |
| 36 | 75.861 | 3,5-Di(p-chlorophenyl)-isoxazole | 0.21 | 43 |

TABLE 2

Ingredient Analysis Table of F2

| Peak | Retention time | Fraction 2 | % Area | Qality |
|---|---|---|---|---|
| 1 | 6.217 | n-Butyl acetate | 3.15 | 72 |
| 2 | 9.252 | 4-Heptanone | 1.42 | 86 |
| 3 | 9.464 | n-Butyl ether | 4.12 | 90 |
| 4 | 11.257 | 3-Methyl-4-heptanone | 1.27 | 95 |
| 5 | 14.08 | Butyl butylate | 2.46 | 90 |
| 6 | 19.303 | 5-phenyl-8-oxa-1-azabicyclo[3.2.1]octane | 1.17 | 59 |
|  |  | 3-phenyl-1,2,4-triazine-5,6(1H,2H)-dione |  | 59 |
| 7 | 23.331 | 1-Methyl-azetidine | 0.89 | 25 |
| 8 | 25.827 | 1,3-bis(1,1-dimethylethyl)-benzene | 0.74 | 9 |
| 9 | 32.004 | Dihexylsulfide | 0.66 | 43 |
| 10 | 33.45 | 1,1'-(1,4-phenylene)bis-ethanone 1-(1,1-dimethylethyl)-3,5-dimethyl-benzene | 0.84 | 86 80 |
| 11 | 35.175 | Iso butanol | 0.52 | 5 |
| 12 | 72.189 | Docosane | 0.87 | 35 |
| 13 | 73.008 | Heptacosane | 1.12 | 14 |
| 14 | 76.738 | 3,5-di-o-methyl-gartanin | 1.35 | 35 |

Example 7

Analysis of Collagen Matrix Metalloproteinase-1 Inhibitory Effect for Each Ingredient of White Rose Petal Extract The inventors tested the MMP-1 inhibitory effect of 36 ingredients analyzed in the F1 and 14 ingredients analyzed in the F2 in order to verify which ingredient of the white rose petal extract had the skin wrinkle alleviation effect.

The test method was performed the same as the method disclosed in Example 3 and as the tested result, it was verified that in 3,5-di-o-methyl-gartanin which was the 14-th fraction of the F2, a particularly excellent inhibition effect of MMP-1 was exhibited.

Example 8

Analysis of Melanin Synthase (Tyrosinase) Inhibitory Effect of 3,5-Di-o-Methyl-Gartanin The inventors performed the test by the same method as the method disclosed in Example 4 in order to verify whether 3,5-di-o-methyl-gartanin showing the excellent MMP-1 inhibitory effect exhibited the tyrosinase inhibitory effect as the melanin synthase.

As a result, it was verified that 3,5-di-o-methyl-gartanin had an excellent tyrosinase inhibition activity.

Example 9

Analysis of Melanin Synthesis Inhibitory Effect of 3,5-Di-o-Methyl-Gartanin

Finally, the inventors observed the melanin synthesis inhibitory effect due to the tyrosinase inhibition activity of the 3,5-di-o-methyl-gartanin through the test method disclosed in Example 5.

As a result, expectedly, the inventors verify that the melanin synthesis of the B16 mouse melanoma cells may be efficiently inhibited by treatment of 3,5-di-o-methyl-gartanin.

Example 10

Analysis of DPPH Reactive Oxygen Scavenging Activity of White Rose Petal Extract for Each Treatment Concentration 2,2-Diphenyl-1-picrylhydrazyl (DPPH) is a free radical which is very stable by itself and a dark violet compound having characteristic light absorption at 517 nm, but is quantitatively discolored by antioxidants having radical scavenging activity. Further, the radical scavenging activity has a correlation with antioxidation activity including inhibition activity of lipid peroxidation and is an experimental method which is widely used for searching antioxidants.

Accordingly, in order to verify DPPH reactive oxygen scavenging activity of the white rose flower, the inventors detected reaction of a DPPH solution, ethanol (EtOH) extract, and each fraction and verified the DPPH reactive oxygen scavenging activity by measuring absorbance at 517 nm by using a microplate-ELISA reader (SpectraMax plus 384, Molecular Devices, CA, USA) after treating vitamin C (Vit.C) as a positive control group.

The DPPH reactive oxygen scavenging activity was measured after treating white rose flower samples with concentrations of 1, 10, 25, and 50 μg/mL respectively, and as a result, it can be seen that the DPPH reactive oxygen scavenging activity is exhibited from the concentration of 10 μg/mL in all the samples (see FIG. 5).

Example 11

Analysis of Metal Ion Catalytic Oxidation Inhibition of White Rose Petal Extract for Each Treatment Concentration As a method of verifying an effect of antioxidants protecting proteins such as bovine serum albumin (BSA) or enzymes from the damage by reactive oxygen species (ROS) by using a metal ion catalytic reaction, in order to verify metal ion catalytic oxidation inhibition activity of the white rose petal extract and the fractions, the following experiment was performed.

First, in order to induce production of free radicals, the metal ion catalytic reaction was used by adding $CuSO_4$ 1 mM and $H_2O_2$ 10 mM and free radicals were produced and then electrophoresed in SDS-polyacrylamide gel for a protection effect of the BSA protein of the extracts and the fractions.

A protein protection effect to the metal ion catalytic free radicals after treating the white rose flower samples with concentrations of 1, 10, 25, and 50 μg/mL was evaluated. As a result, it can be seen that in an ethanol (EtOH) extract, a protein protection effect by the metal ion catalytic free radicals is exhibited from the concentration of 10 μg/mL, whereas in butanol (BuOH) and Fraction 2, the protection effect is observed from the concentration of 1 μg/mL (see FIG. 6).

Example 12

Analysis of Tyrosinase Activity Inhibition In Vitro of White Rose Petal Extract for Each Treatment Concentration The inventors mixed the white rose flower fractions with 100 mM of a sodium phosphate buffer (pH 6.5), L-tyrosine, and mushroom tyrosinase and reacted at 37° C. for 30 minutes, and thereafter, measured tyrosinase inhibition activity through intensity after photographing by using a OLYMPUS CKX 41 (Olympus, Tokyo, Japan).

The tyrosinase inhibition activity after treating the white rose flower samples with concentrations of 10 and 25 μg/mL was measured. As a result, it can be seen that the tyrosinase inhibition activity is exhibited in all the samples and particularly, in butanol (BuOH) and Fraction 2, the tyrosinase inhibition activity is exhibited at a similar level to vitamin C as a positive control group (see FIG. 7).

Through the above result, the inventors experimentally verified that the white rose petal extract had the skin whitening and skin wrinkle alleviation effects and verified that the white rose petal extract, particularly, the 3,5-di-o-methyl-gartanin exhibited an excellent effect in skin whitening and skin wrinkle alleviation by the MMP-1 activity and tyrosinase activity inhibition effects. Accordingly, the cosmetic composition including the white rose petal extract or the 3,5-di-o-methyl-gartanin can be utilized as an important ingredient for functional cosmetics for skin whitening and skin wrinkle alleviation.

Hereinafter, as cosmetic Formulation Examples of the present invention, Lotion, essence, body cleanser, and the like including a white rose extract (alternatively, 3,5-di-o-methyl-gartanin) as an active ingredient of the present invention will be exemplified. However, the formulation of the cosmetic material of the present invention is not necessarily limited thereto.

[Formulation Example 1] Skin Lotion

A skin lotion was prepared by a general method by adding the following ingredients and contents.

White rose extract (alternatively, 3,5-di-o-methyl-gartanin)—2.0 wt %, 1,3-butylene glycol—5.2 wt %, oleyl alcohol—1.5 wt %, ethanol—3.2 wt %, polysorbate 20-3.2 wt %, benzophenone 9-2.0 wt %, carboxyl vinyl polymer—1.0 wt %, glycerine—3.5 wt %, flavor—small amount, preservative—small amount, and purified water—residual amount %

[Formulation Example 2] Essence

An essence was prepared by a general method by adding the following ingredients and contents.

White rose extract (alternatively, 3,5-di-o-methyl-gartanin)—2.0 wt %, cetostearyl alcohol—1.0 wt %, glyceryl monostearate—0.8 wt %, sorbitan monostearate—0.3 wt %, propylparaben—0.1 wt %, polysorbate 60-1.0 wt %, mineral oil—5.0 wt %, cyclomethicone—3.0 wt %, dimethicone—0.5 wt %, allantoin—0.1 wt %, glycerine—5.0 wt %, alcohol—2 wt %, propylene glycol—3.0 wt %, flavor—small amount, preservative—small amount, and purified water—residual amount %

[Formulation Example 3] Body Cleanser

A body cleanser was prepared by a general method by adding the following ingredients and contents.

White rose extract (alternatively, 3,5-di-o-methyl-gartanin)—2.0 wt %, alkylether saccharate salt (30%)—30.0 wt %, alkylether sulfosuccinic acid salt (30%)—20.0 wt %, alkylamido betaine (30%)—5.0 wt %, propylene glycol—5.0 wt %, betaine—5.0 wt %, lauramide DEA—4.0 wt %, cellulose gum—0.05 wt %, hydrolyzed protein—0.1 wt %, citric acid—small amount, NaCl—small amount, flavor—small amount, preservative—small amount, and purified water—residual amount %

Hereinabove, the preferred exemplary embodiments of the present invention have been primarily described. It is understood to those skilled in the art that the present invention may be implemented as a modified form without departing from an essential characteristic of the present invention. Therefore, the disclosed exemplary embodiments should be considered from not a limitative viewpoint but an explanatory viewpoint. It should be construed that the scope of the present invention should be interpreted by not the above description but the appended claims and all differences in the equivalent range thereto are included in the present invention.

The invention claimed is:

1. A cosmetic composition for skin whitening or skin wrinkle alleviation, the cosmetic composition comprising a white rose flower ethyl acetate fraction as an active ingredient.

2. The cosmetic composition of claim 1, wherein the white rose flower ethyl acetate fraction prevents melanin production by suppressing or inhibiting activity of tyrosinase.

3. The cosmetic composition of claim 1, wherein the white rose flower ethyl acetate fraction improves skin elasticity by suppressing or inhibiting activity of MMP-1.

4. The cosmetic composition of claim 1, wherein the composition is formulated by at least one selected from the group consisting of skin lotion, skin softener, skin toner, astringent, lotion, milk lotion, moisturizing lotion, nutrition lotion, massage cream, nourishing cream, moisturizing cream, hand cream, essence, nutrition essence, pack, soap, shampoo, cleansing foam, cleansing lotion, cleansing cream, body lotion, body cleanser, emulsion, lipstick, makeup base, foundation, pressed powder and loose powder.

5. A cosmetic composition for skin whitening or skin wrinkle alleviation, the cosmetic composition comprising a white rose flower ethyl acetate fraction as an active ingredient,
wherein the white rose flower ethyl acetate fraction is characterized by being prepared as in steps 1 to 3 below:
extracting white rose flower with an aqueous ethanol solution (step 1);
fractionating the ethanol aqueous solution extract of step 1 with hexane, and separating the hexane fraction from residue generated thereby (step 2); and
fractionating the residue of step 2 with ethyl acetate, and separating the ethyl acetate fraction from residue generated thereby (step 3), thereby obtaining the white rose flower ethyl acetate fraction.

* * * * *